(12) United States Patent
Löffert et al.

(10) Patent No.: US 8,435,774 B2
(45) Date of Patent: May 7, 2013

(54) ENHANCING REACTIVATION OF THERMOSTABLE REVERSIBLY INACTIVATED ENZYMES

(75) Inventors: Dirk Löffert, Duesseldorf (DE); Ralf Peist, Hilden (DE); Patrick Baumhof, Hilden (DE)

(73) Assignee: QIAGEN GmbH, Hilden (DE)

( * ) Notice: Subject to any disclaimer, the term of this patent is extended or adjusted under 35 U.S.C. 154(b) by 1178 days.

(21) Appl. No.: 11/821,173

(22) Filed: Jun. 22, 2007

(65) Prior Publication Data

US 2008/0003656 A1  Jan. 3, 2008

Related U.S. Application Data

(60) Provisional application No. 60/817,043, filed on Jun. 28, 2006, provisional application No. 60/852,804, filed on Oct. 19, 2006.

(51) Int. Cl.
*C12N 9/00* (2006.01)

(52) U.S. Cl.
USPC .......................................... 435/183; 435/194

(58) Field of Classification Search ................... 435/183
See application file for complete search history.

(56) References Cited

U.S. PATENT DOCUMENTS

| 5,677,152 A | 10/1997 | Birch et al. ................... 435/91.2 |
| 5,773,258 A | 6/1998 | Birch et al. ................... 435/91.2 |
| 6,183,998 B1 | 2/2001 | Ivanov et al. ................ 435/91.2 |

*Primary Examiner* — Ralph Gitomer
*Assistant Examiner* — Robert Yamasaki
(74) *Attorney, Agent, or Firm* — Ballard Spahr LLP (57) ABSTRACT

Disclosed are methods for the enhancement of the reactivation of thermostable reversibly inactivated enzymes comprising reactivating at least one thermostable reversibly inactivated enzyme in the presence of one or more nitrogen containing compounds.

2 Claims, 4 Drawing Sheets

ENHANCING REACTIVATION OF THERMOSTABLE REVERSIBLY INACTIVATED ENZYMES

CROSS-REFERENCE TO RELATED APPLICATIONS

This application claims the benefit of priority to U.S. Provisional Application Nos. 60/817,043, filed Jun. 28, 2006, and 60/852,804, filed Oct. 19, 2006, both of which are incorporated by this reference in their entireties.

BACKGROUND

Some molecular biology methods demand enzymes that can be activated in a controlled manner while being already contained in the reaction. This allows starting sequential enzymatic procedures in the same reaction container at predefined time points or avoiding the generation of undesired side products due to premature start of the enzymatic reaction. For the use of chemically modified thermostable enzymes, two such modifications have been described for thermostable DNA polymerases (see U.S. Pat. Nos. 5,677,152; 5,773,258; and 6,183,998, which are incorporated by reference herein in their entireties). Such modifications can also be employed for other thermostable enzymes since amino acids become modified by these chemicals that are contained in all enzymes and are often involved in the catalytic centre of enzymes such as amino acids carrying a free $NH_2$-group. Furthermore, U.S. Pat. No. 6,183,998 teaches the crosslinking of enzyme molecules by aldehydes, which is generically suitable to modify any thermostable enzyme. The activity of such chemically modified enzymes becomes restored by a heat incubation step that breaks the covalent bonds to the amino acid residues thereby restoring the catalytic activity of the enzyme. However, depending on the inactivation procedure or the modifier concentration chosen, enzyme activity is restored only at a slow rate.

The inventors have discovered that nitrogen-containing compounds surprisingly enhance enzyme activity of chemically modified enzymes while they have no effect on the unmodified enzyme. Thus, this invention describes for the first time a mechanism that enhances the reactivation of chemically modified enzymes, which is suitable in many applications, e.g., to increase speed of the enzymatic reaction.

SUMMARY

In accordance with the purposes of the disclosed materials, compounds, compositions, articles, and methods, as embodied and broadly described herein, the disclosed subject matter, in one aspect, relates to compounds and compositions and methods for preparing and using such compounds and compositions. In a further aspect, the disclosed subject matter relates to the use of one or more nitrogen containing compounds to enhance reactivation of reversibly inactivated thermostable enzymes.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitute a part of this specification, illustrate several aspects described below.

DETAILED DESCRIPTION

The materials, compounds, compositions, articles, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an enzyme" includes mixtures of two or more such enzymes, reference to "the primer" includes mixtures of two or more such primers, and the like.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol, as described herein. A "lower alkyl" group is an alkyl group containing from one to six carbon atoms.

The term "alkoxy" as used herein is an alkyl or cycloalkyl group bonded through an ether linkage; that is, an "alkoxy" group can be defined as —$OA^1$ where $A^1$ is alkyl or cycloalkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol, as described herein.

The term "acyl" means derivatives of the corresponding acids comprising 10 or less continuous C-atoms. These acid moieties can carry additional alkyl groups or functional groups like hydroxyl, amino, carboxyl, sulfonic acid, ester or ether groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, boronic acid, ester, ether, halide, hydroxy, ketone, azide, nitro, hydroxamate, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl. The term "phenyl" is included within the meaning of aryl and means a benzyl moiety, which can carry additional alkyl chains (comprising 4 or less continuous C-atoms) or functional groups like hydroxyl, amino, nitro, carboxyl, sulfonic acid, esters, ether or halogen groups, attached to the ring.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein. The term "amino alkyl" means an amino group with an alkyl moiety. The term "alkyl" is defined above. Equally, derivatives of amino alkyl correspond to the derivatives of alkyl groups.

The term "azole" as used herein is a substituted or unsubstituted or fused five-membered ring containing at least one nitrogen atom in the ring.

The term "carboxylic acid" as used herein is represented by the formula —C(O)OH.

The term "ester" as used herein is represented by the formula —$OC(O)A^1$ or —$C(O)OA^1$, where $A^1$ can be a substituted or unsubstituted alkyl, cycloalkyl, alkenyl, cycloalkenyl, alkynyl, cycloalkynyl, aryl, or heteroaryl group as described herein.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein.

The term "halide" or "halogen" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A$, —$OS(O)_2A^1$, or —$OS(O)_2OA^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^1$, where A$^1$ and A$^1$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^1$, where A$^1$ and A$^1$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," and "X," as used herein can, independently, possess one or more of the groups listed above. For example, if R$^1$ is an alkyl group, one of the hydrogen atoms of the alkyl can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Reference will now be made in detail to specific aspects of the disclosed materials, compounds, compositions, articles, and methods, examples of which are illustrated in the accompanying Examples and Figures.

Methods and Compositions

The present invention provides a method to enhance reactivation of reversibly inactivated thermostable enzymes. In particular, the disclosed methods involve the use of nitrogen containing compounds characterized by the following Formula 1-6 where each X is, independent of the others, CH, CR, N, O, or S; and each R is, independent of the others, H, substituted or unsubstituted alkyl, alkenyl, alkynyl, alkoxyl, or aryl, a hydroxyl, amino, nitro, carboxylic acid, ester, sulfonic acid, ether, or halogen group. As disclosed herein, these compounds, including mixtures thereof, can be employed to enhance reactivation of thermostable reversibly inactivated enzymes.

In various examples, disclosed herein are methods for the enhancement of the reactivation of thermostable reversibly inactivated enzymes that comprise reactivating at least one thermostable reversibly inactivated enzyme in the presence of a nitrogen-containing compound. Specific examples of nitrogen containing compounds suitable for use herein include, but are not limited to, an azole. Suitable azoles can comprise a nitrogen-containing 5-membered cyclic compound having Formula 1, Formula 1 where each X can be, independent of the others, CH, CR, or N; and R can be H, substituted or unsubstituted alkyl, alkenyl, alkynyl, alkoxyl, or aryl group, a hydroxyl, amino, nitro, carboxylic acid, ester, sulfonic acid, ether, or halogen group.

In another example, a suitable azole can comprise a nitrogen-containing 5-membered cyclic compound having Formula 2, Formula 2 where each X can be, independent of the others, CH, CR, N, O, or S; and each R can be, independent of the others, H, substituted or unsubstituted alkyl, alkenyl, alkynyl, alkoxyl, or aryl group, a hydroxyl, amino, nitro, carboxylic acid, ester, sulfonic acid, ether, or halogen group. In a further example, each X can be, independent of the others, CH or N in any combination.

In yet a further example, a suitable azole can comprise a nitrogen-containing bicyclic compound having Formula 3, Formula 3 where each X can be, independent of the others, CH, CR, N, O, or S; and each R can be independent of the others, H, substituted or unsubstituted alkyl, alkenyl, alkynyl, alkoxyl, or aryl group, a hydroxyl, amino, nitro, carboxylic acid, ester, sulfonic acid, ether, or halogen group.

Also disclosed herein are methods for the enhancement of the reactivation of thermostable reversibly inactivated enzymes that comprise reactivating at least one thermostable reversibly inactivated enzyme in the presence of a compound comprising a pyridine having Formula 4, Formula 4 where each X can be, independent of the others, CH, CR, or N; and R can be a hydroxyl, amino, thiol, or amino alkyl group, or derivatives thereof.

Still further, disclosed herein are methods for the enhancement of the reactivation of thermostable reversibly inactivated enzymes that comprise reactivating at least one thermostable reversibly inactivated enzyme in the presence of a compound comprising an N-hydroxide having Formula 5, Formula 5 where each R can be, independent of the other, H, substituted or unsubstituted alkyl, alkenyl, alkynyl, alkoxyl, or aryl group, or an acyl group or derivatives thereof.

In yet a further example, disclosed herein are methods for the enhancement of the reactivation of thermostable reversibly inactivated enzymes that comprise reactivating at least one thermostable reversibly inactivated enzyme in the presence of a compound comprising a hydrazine having Formula 6, Formula 6 where each R can be, independent of the other, H, substituted or unsubstituted alkyl, alkenyl, alkynyl, alkoxyl, or aryl group, or an acyl group or derivatives thereof.

In another example, disclosed herein are methods for the enhancement of the reactivation of thermostable reversibly inactivated enzymes that comprise reactivating at least one thermostable reversibly inactivated enzyme in the presence of an ammonium salt. An ammonium salt is any compound that contains a positively charged nitrogen species of the formula $^+NR_4$, where each R can be, independent of the others, H, substituted or unsubstituted alkyl, alkenyl, alkynyl, alkoxyl, or aryl, a hydroxyl, amino, nitro, carboxylic acid, ester, sulfonic acid, ether, or halogen group, and a negatively charged inorganic counterion, organic counterion, a metal oxide counterion, or a metal complex counterion counterion.

Suitable positively charged nitrogen species for the ammonium salts are $NH_4$ and tetraalkyl ammonium. Suitable counterions in the ammonium salts can have one or more negative charges. Examples of suitable counterions include, but are not limited to, inorganic counterions like halogens (e.g., $F^-$, $Cl^-$, $Br^-$, and $I^-$), pseudohalogenes (e.g., $SCN^-$ and $OCN^-$), perchlorate ($ClO_4^-$), chlorate ($ClO_3^-$), chlorite ($ClO_2^-$), hypochlorite ($ClO^-$), bromate ($BrO_3^-$), periodate ($IO_4^-$), sulfide ($S^{2-}$), sulfate ($SO_4^{2-}$), sulfite ($SO_3^{2-}$), bisulfate ($HSO_4^-$), phosphide ($P^{3-}$), phosphate ($PO_4^{3-}$), hydrogen phosphate ($HPO_4^{2-}$), dihydrogen phosphate ($H_2PO_4^-$), phosphite ($PO_3^{2-}$), nitride ($N^{3-}$), nitrate ($NO^{3-}$), nitrite ($NO^{2-}$), hydroxide ($OH^-$), peroxide ($O_2^{2-}$), hexaflourophosphate ($PF_6^-$), and permanganate ($MnO_4^-$).

Further examples of suitable counterions include, but are not limited to, organic counterions like carbonate ($CO_3^{2-}$), bicarbonate ($HCO_3^-$), formate ($CHO_2^-$), acetate ($CH_3CO_2^-$) and other alkyl carboxylates ($RCO_2^-$, where R is alkyl, e.g., propionate, buterate, etc.), oxylate ($C_2O_4^{2-}$), tartrate and malate ($C_4H_4O_6^{2-}$), citrate ($C_6H_5O_7^{3-}$), and benzoate ($C_6H_5CO_2^-$).

Other suitable counterions include, but are not limited to, metal oxides and metal complexes. Examples of metal oxides and metal complexes include orthovanadate, molybdate ($Mo_7O_{24}$), hexacyanoferrate ($FeCN_6$)$^{4-}$, and cerium nitrate.

Any of the counterions disclosed herein can be combined with any of the ammonium species disclosed herein to form an ammonium salt. Some specific examples of suitable ammonium salts include, but are not limited to, ammonium chloride ($NH_4Cl$), ammonium dihydrogen phosphate ($NH_4H_2PO_4$), ammonium biphosphate (($NH_4)_2HPO_4$), ($NH_4)_3PO_4$, ($NH_4)_4(Fe(CN)_6)$, ammonium acetate ($NH_4CH_3CO_2$), ammonium carbonate ($NH_4)_2CO_3$), ammonium molybdate ($NH_4Mo_7O_{24}$), ammonium perchlorate ($NH_4ClO_4$), ammonium citrate (($NH_4)_3C_6H_5O_7$), ammonium benzoate ($NH_4C_6H_5CO_2$), and ammonium phosphate (($NH_4)_3PO_4$).

It is understood that some adjustments can be made to the methods disclosed herein. For example, if a counterion of the ammonium salt chelates Mg from the reaction, which is required by the enzyme as a co-factor, the salt can still provide the same effect on reactivation. However, one would have to increase the Mg concentration of the reaction to compensate for the chelating effect of the counterion. Also, if a counterion has an inhibitory effect on the enzyme, one can optimize for a concentration that is effective but still not inhibitory.

In one particular aspect, the ammonium salt can be used with any of the azoles, pyrimidines, N-hydroxylamines, or hydrazines disclosed herein. As is discussed more fully below, the use of an ammonium salt, as disclosed herein, with any of the other nitrogen containing compounds disclosed herein can result in a synergistic effect.

In the methods disclosed herein, the azoles, pyrimidines, N-hydroxides, and hydrazines, disclosed herein can be present at a concentration of from about 0.5 mM to about 1 M, e.g., about 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 mM, where any of the stated values can form an upper or lower endpoint of a range. For the ammonium salts, the ammonium species can be present at any of the concentrations just listed.

In certain examples, the ammonium compound is not ammonium citrate, di-ammonium hydrogen phosphate, ammonium benzoate, ammonium carbonate, or ammonium sulfate.

The disclosed methods can be employed in all applications involving manipulation of nucleic acids, such as amplification, ligation, exonucleolytic or endonucleolytic reactions, or nucleic acid topology changing enzymatic reactions, wherein the inactivated enzymes become reactivated by incubating the reaction mixture prior or as part of the intended enzymatic reaction at an elevated temperature in the presence of nitrogen-containing compounds according to the description.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

As model system to exemplify the invention, hot start PCR was chosen with two commercially available enzymes. This shows the generic suitability of the invention because both polymerases were inactivated with a different chemical modifier. AmpliTaq Gold (Applied Biosystems) is chemically inactivated using dicarboxylic acid anhydride whereas HotStarTaq (QIAGEN) is chemically inactivated using formaldehyde. Hot start PCR was chosen as model system for the following reasons: (i) The polymerase chain reaction is a widely used molecular biology application and thus illustrates the economical importance of the invention, (ii) due to the inherent high efficiency of the reaction, PCR is a good model system to show that the substances used in the invention do not influence reactions that contain an unmodified enzyme and secondly can even further enhance the efficiency of such reaction even further if a chemically modified enzyme is contained.

To easily demonstrate the increase of enzyme reactivation efficiency, real-time PCR was chosen. In real-time PCR, the enzymatic reaction is continuously monitored by measuring fluorescence signals throughout the reaction. Double-stranded DNA molecules are generated during the PCR reaction. These PCR products are detected by using SYBR Green I fluorescent dye that binds selectively to dsDNA only. Thus, an increase of fluorescence indicates an increase in PCR product amount and thus activity of the DNA polymerase contained in the reaction. Once the total fluorescence significantly increases above the fluorescent background signal, the so-called $C_T$ value is reached. Thus, the $C_T$ value is a measurement for the enzyme activity contained in the reaction: Low $C_T$ values indicate high enzyme activity and high $C_T$ values represent lower enzyme activity residing in the reaction.

Yet, another example shows a titration of one of the chosen substances (Triazole) and its effect on increasing the enzyme activity in PCR by the generation of concentration dependent PCR product yields.

Example 1

A SYBR Green I based PCR reaction was conducted in the presence of unmodified Taq DNA Polymerase (QIAGEN) serving as a control reaction, using HotStarTaq DNA polymerase (QIAGEN) or AmpliTaq Gold (Applied Biosystems). Each reaction contained 0.625 units of the respective DNA polymerase, 1×PCR reaction buffer of the respective DNA polymerase, 200 µM of each dNTP, 0.5 µM primer A: 5'-GTC ACC TTC ACC GTT CCA GT-3' (SEQ ID NO:1), 0.5 µM primer B: 5'-CTC TTC CAG CCT TCC TTC CT-3' (SEQ ID NO:2), PCR grade water and in case of testing nitrogen-containing compounds as example 100 mM Triazole, final concentration. Each reaction contained 10 ng human genomic DNA as amplification substrate. PCR reactions were started with an initial enzyme activation step at 95° C. for 5 minutes followed by 50 cycles: 94° C. for 15 seconds and 60° C. for 60 seconds. Average $C_T$ values were determined from triplicate reactions comparing reactions without the addition of Triazole and with 100 mM Triazole.

| Enzyme | Average $C_T$ value without Triazole | Average $C_T$ value with 100 mM Triazole |
|---|---|---|
| Taq (unmodified) | 21.0 | 21.3 |
| HotStarTaq | 42.3 | 35.9 |
| AmpliTaq Gold | 27.6 | 25.6 |

Result: While the addition of Triazole showed no effect on the enzyme activity when using unmodified Taq DNA polymerase, reactions containing Triazole showed clearly higher enzyme activity when using both chemically modified enzymes, HotStarTaq DNA Polymerase and AmpliTaq Gold.

Example 2

Figure 1:
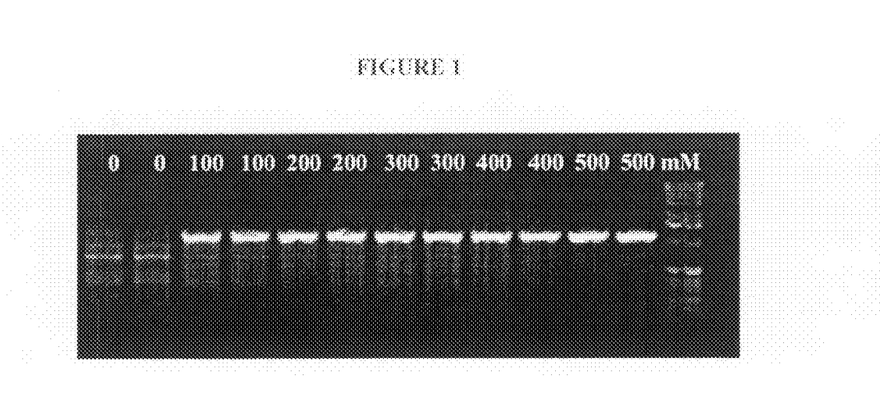
FIG. 1 is an agarose gel from a fast PCR reaction with varying concentrations of Triazole.

A fast PCR reaction with significantly shortened cycling times was conducted containing the chemically modified HotStarTaq DNA Polymerase in the absence of Triazole and in the presence of increasing Triazole concentrations. Each PCR reaction contained 1.5 units HotStarTaq DNA Polymerase, 10 ng template human genomic DNA, 200 µM of each dNTP, 0.5 µM primer A: 5'-CAC ACA GCG ATG GCA GCT ATG C-3' (SEQ ID NO:3), 0.5 µM primer B: 5'-CCC AGT GAT GGG CCA GCT C-3' (SEQ ID NO:4), PCR grade water and in case of testing nitrogen-containing compounds as example 100 mM, 200 mM, 300 mM, 400 mM and 500 mM Triazole, final concentration. PCR reactions were started with an initial enzyme activation step at 95° C. for 5 minutes followed by 35 cycles: 96° C. for 5 seconds, 60° C. for 5 seconds and 68° C. for 30 seconds. PCR products were analysed on a 1% TAE agarose gel (FIG. 1).

Result: The fast PCR in the absence of Triazole shows only generation of unspecific side products whereas the addition of either concentration of Triazole significantly improves enzyme activity generating the desired PCR product even under fast cycling PCR condition.

Example 3

A SYBR Green I based PCR reaction was conducted in the presence of unmodified Taq DNA Polymerase (QIAGEN) serving as a control reaction and HotStarTaq DNA polymerase (QIAGEN). Each reaction (20 μL reaction volume) contained QuantiTect SYBR Green PCR Master Mix without HotStarTAQ DNA Polymerase and without $(NH_4)_2SO_4$. 1.0 units of the respective DNA Polymerase and 0.5 μM primer A: 5'-GTC ACC TTC ACC GTT CCA GT-3' (SEQ ID NO:5), 0.5 μM primer B: 5'-CTC TTC CAG CCT TCC TTC CT-3' (SEQ ID NO:6), PCR grade water and in case of testing ammonia-containing compounds the different ammonium compounds (for ammonia compound and concentration see table). Each reaction contained 10 ng human genomic DNA as amplification substrate. PCR reactions were started with an initial enzyme activation step at 95° C. for 10 minutes (witch is 5 minutes shorter than the time described in the QIAGEN QuantiTect SYBR Green protocol) followed by 40 cycles: 94° C. for 15 seconds and 55° C. for 39 seconds and 72° C. for 40 seconds. Average $C_T$ values were determined from triplicate reactions comparing reactions without the addition of ammonia compounds and with ammonia compounds in different concentrations (for ammonia compound and concentration see FIG. 2).

Figure 2:
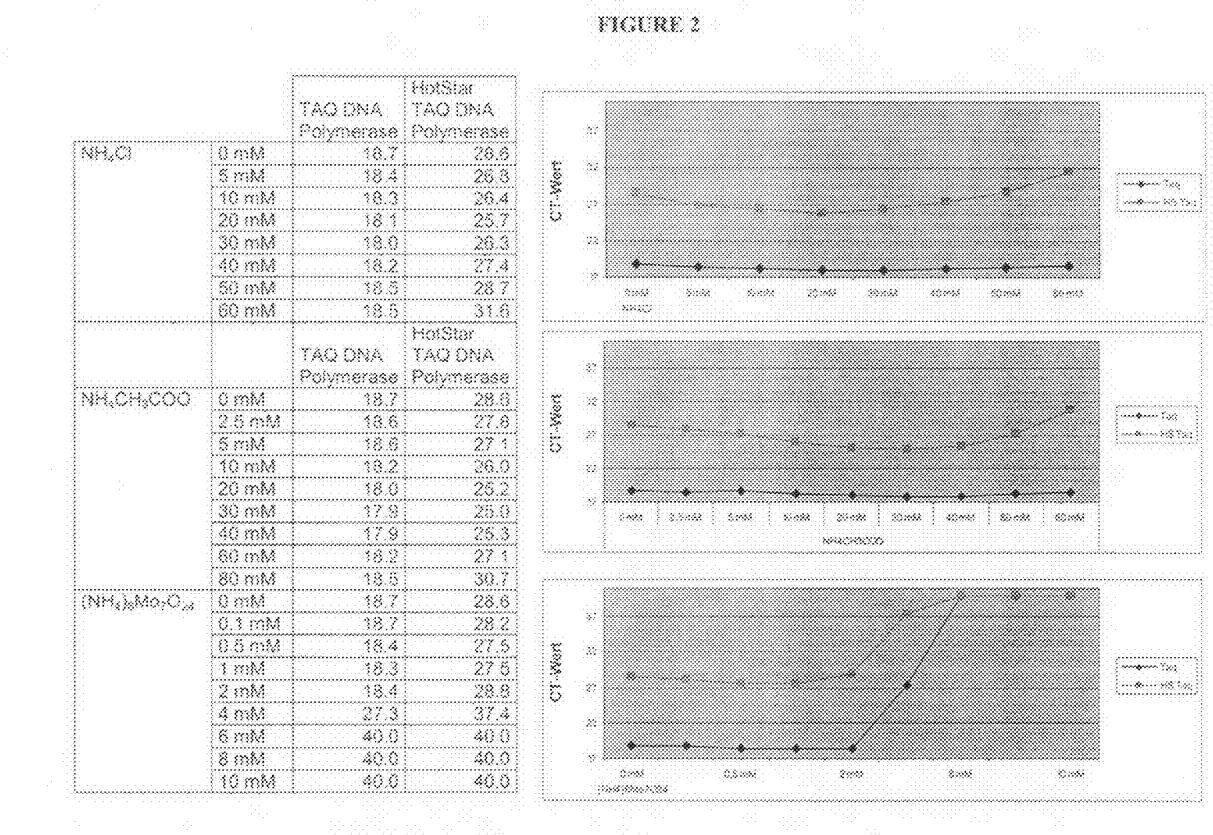
FIG. 2 is a group of tables and accompanying graphs, each table showing average $C_T$ values from reactions with varying concentrations of a particular ammonia compound.

Result: While the addition of ammonia compounds showed no effect (or inhibition at high concentrations) on the enzyme activity when using unmodified Taq DNA polymerase, reactions containing ammonia compounds showed clearly higher enzyme activity when using a chemically modified enzyme like HotStarTaq DNA Polymerase.

Example 4

Figure 3:
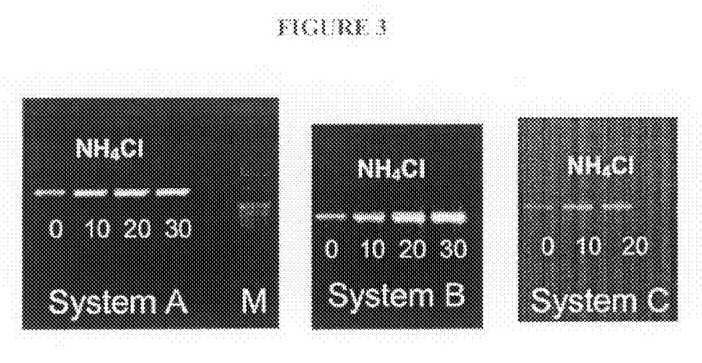
FIG. 3 is a group of three agarose gels from three fast PCR reactions with varying concentrations of ammonium chloride.

A fast PCR reaction with significantly shortened cycling times was conducted containing the chemically modified HotStarTaq DNA Polymerase in the absence (control reaction; 0 mM ammonium chloride) and presence of increasing ammonium chloride concentrations (10, 20, and 30 mM in the final reaction mixture). Each PCR reaction contained 1.5 units HotStarTaq DNA Polymerase, 10 ng template human or mouse genomic DNA, 200 μM of each dNTP, 0.5 μM of each primer for each different PCR assay (Assay A, primer A1: 5'-GCT TGA GCA ACC TGG CTA AGA TAG AGG-3' (SEQ ID NO:7), primer A2: 5'-GAG TTA GCA GGA GGC TGG ATG CAG ATG-3' (SEQ ID NO:8); Assay B, primer B 1: 5'-CCA CAA TGG ACA TCA CAC AAG TGA G-3' (SEQ ID NO:9), primer B2: 5'-GAT CTT TCT GCC CAG ATA CCA TTC G-3' (SEQ ID NO:10); Assay C, primer C1: 5'-CCT TGC CTT AGA TGT GTC GGC A-3' (SEQ ID NO:11), primer C2: 5'-CCC AAA CCC AAC CCA TAC ACA C-3' (SEQ ID NO:12)) and PCR grade water. PCR reactions were started with an initial enzyme activation step at 95° C. for 5 minutes followed by 35 cycles: 96° C. for 5 seconds, 60° C. for 5 seconds and 68° C. for 30 seconds/kb PCR product size. PCR products were analysed on a 1% TAE agarose gel. M: DNA size ladder (FIG. 3).

Result: Addition of increasing amounts of ammonium chloride leads to an increase of overall enzyme activity of the chemically inactivated enzyme when compared to the reaction that do not contain any ammonia compound.

Example 5

Figure 4:
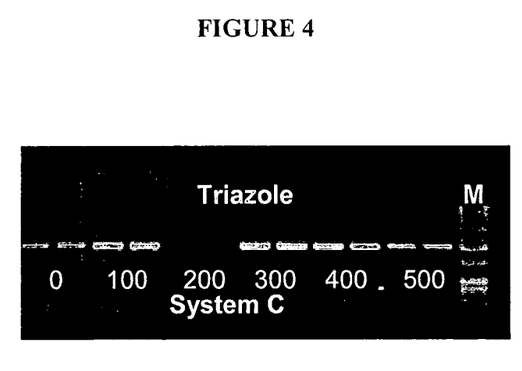
FIG. 4 is an agarose gel from a fast PCR reaction in the presence of ammonium chloride and varying concentrations of Triazole.

In order to demonstrate the synergistic cumulative effect of a combination of an ammonia compound and an azole, a fast PCR reaction with significantly shortened cycling times was conducted containing the chemically modified HotStarTaq DNA Polymerase in the presence of 20 mM ammonium chloride in the absence (control reaction 0) and presence of increasing of Triazole concentrations (100, 200, 300, 400 and 500 mM in the final reaction mixture). System C shown in Example 4 was chosen as model system. Each PCR reaction contained 1.5 units HotStarTaq DNA Polymerase, 10 ng template human genomic DNA, 200 μM of each dNTP, 0.5 μM of each primer A: 5'-CCT TGC CTT AGA TGT GTC GGC A-3' (SEQ ID NO:11), primer B: 5'-CCC AAA CCC AAC CCA TAC ACA C -3' (SEQ ID NO:12), and PCR grade water. PCR reactions were started with an initial enzyme activation step at 95° C. for 5 minutes followed by 35 cycles: 96° C. for 5 seconds, 60° C. for 5 seconds and 68° C. for 45 seconds. PCR products from duplicate reactions were analysed on a 1% TAE agarose gel. M: DNA size ladder. Due to a handling error during PCR setup, the reaction indicating the assay in the presence of 200 mM Triazole shows no result (FIG. 4).

Result: Compared to the reaction containing only 20 mM ammonium chloride in the absence of Triazole, addition of Triazole shows a clear benefit for the enzyme activity of the chemically modified enzyme. Although the effect of Triazole starts to become less significant at very high concentration of 500 mM, the activity is still higher than in the reaction without Triazole. This example indicates that a combination of ammonia compounds and azole can work synergistically to enhance enzyme activity of a chemically modified enzyme.

Additionally tested compounds that showed no improvement were $C_6H_{17}N_3O_7$ (ammonium citrate), $H_9N_2O_4P$ (diammonium hydrogen phosphate), $C_7H_9NO_2$ (ammonium benzoate), $(NH_4)_2CO_3$ (ammonium carbonate), $(NH_4)_2SO_4$ (ammonium sulfate).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for the enhancement of the reactivation of thermostable reversibly inactivated DNA polymerase, comprising: reactivating at least one thermostable reversibly inactivated DNA polymerase in the presence of triazole.

2. The method of claim 1, wherein reactivating is also in the presence of an ammonium salt.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 1
gtcaccttca ccgttccagt                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 2
ctcttccagc cttccttcct                                              20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 3
cacacagcga tggcagctat gc                                           22

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 4
cccagtgatg ggccagctc                                               19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 5
gtcaccttca ccgttccagt                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 6
ctcttccagc cttccttcct                                              20

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 7
gcttgagcaa cctggctaag atagagg                                      27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 8
gagttagcag gaggctggat gcagatg                                      27

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 9
ccacaatgga catcacacaa gtgag                                        25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 10
gatctttctg cccagatacc attcg                                        25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 11
ccttgcctta gatgtgtcgg ca                                           22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 12
cccaaaccca acccatacac ac                                           22